(12) United States Patent
Burek

(10) Patent No.: US 8,372,446 B2
(45) Date of Patent: Feb. 12, 2013

(54) AVIAN FEED COMPOSITION

(76) Inventor: Susan Burek, Willis, MI (US)

( * ) Notice: Subject to any disclaimer, the term of this patent is extended or adjusted under 35 U.S.C. 154(b) by 389 days.

(21) Appl. No.: 12/416,181

(22) Filed: Apr. 1, 2009

(65) Prior Publication Data

US 2010/0255128 A1    Oct. 7, 2010

(51) Int. Cl.
*A61K 36/8962* (2006.01)
*A61K 36/00* (2006.01)
(52) U.S. Cl. .................................... 424/725; 424/754
(58) Field of Classification Search ............... 424/725, 424/754
See application file for complete search history.

(56) References Cited

U.S. PATENT DOCUMENTS

| 7,011,853 B2 | 3/2006 | Ruepp |
| 7,037,519 B1 | 5/2006 | Humphrey |
| 2005/0013921 A1 | 1/2005 | Peticca |
| 2007/0098733 A1 * | 5/2007 | Emery et al. .............. 424/184.1 |

FOREIGN PATENT DOCUMENTS

WO    2004/091307 A2    10/2004

OTHER PUBLICATIONS

The Hindustan Times: Garlic Pills Not a Viable Option to Fight Colds Yet; New Delhi, Jul. 8, 2999; 2 pages from ProQuest database.*
US Fed News Service: Avian Bacterium More Dangerous Than Believed; Washington DC, Jun. 19, 2009, 2 pages from ProQuest database.*
Guaralnik et al. Limitations of Current Prophylaxis Against Influenza Virus Infection; American Journal of Therapeutics 14, 449-454 (2007).*
Vanderhaeghen et al.: Methicillin-Resistant *Staphylococcus aureus* (MRSA) in Food Production Animals; Infection; May 2010, vol. 138, Issue 5, p. 606, 20 pages.*
Jacob, Jacquie, Pescatore, Tony, Natural remedies for poultry diseases common in 'natural' and 'organic' flocks, www2.ca.uky.edu/afspoultry-iles/pubs/Natural_remedies.pdf, pp. 1-6, issued Feb. 2011.
Pourali, Mostafa, Mirghelenj, S.A., Kermanshahi, H., Effects of Garlic Powder on Productive Performance and Immune Response of Broiler Chickens Challenged with Newcastle Disease Virus, Global Veterinaria 4; pp. 616-621, IDOSI Publications, 2010.
Willis, W.L., King, K., Iskhuemhen, O.S., and Ibrahim, S.A., Administration of mushroom extract to broiler chickens for bifidobacteria enhancement and *Salmonella* reduction, pp. 658-664, Poultry Science Association, Inc., 2009.

* cited by examiner

*Primary Examiner* — Patricia Leith
(74) *Attorney, Agent, or Firm* — Dobrusin & Thennisch PC

(57) ABSTRACT

The invention herein contemplates an avian feed composition and a method for administering and customizing the feed composition for one or more birds. The feed composition aids in preventing infection and illness including parasitic infestation.

12 Claims, No Drawings

AVIAN FEED COMPOSITION

FIELD OF THE INVENTION

This invention relates to an avian feed composition providing increased health benefits and including anti-viral and anti-bacterial characteristics. This invention further relates to methods for promoting balanced avian health functions utilizing natural medicinal herbal compositions that operate in a trophorestorative manner.

BACKGROUND OF THE INVENTION

Avian health care can become much more manageable by adhering to certain dietary principles to prevent the development of disease. Once a bird becomes ill, it is much more difficult to provide care, as the health issue must be correctly diagnosed and treated with the correct type and amount of medication. For self-preservation, birds instinctually hide their weaknesses and may only leave a short window of time to respond to an illness and appropriately intervene. The end result may include costly veterinary services or at worst, fatality. When considering those alternatives, preventative care becomes a more reasonable and common sense approach.

The avian species depends heavily on their digestive systems to stay nourished and healthy. Birds have high metabolisms, and their digestive systems are faster and more efficient than other animals. Most birds cannot afford to store heavy food materials within their bodies for long periods, and they usually need a constant supply of nutrients to sustain activity.

The avian large and small intestines are often populated with both beneficial bacterial microflora and opportunistic and pathogenic bacteria. The pathogenic bacteria come from what birds may pick up from contaminated food or water, bird droppings, or other infected sources in the environment. The microflora are carefully balanced and that balance is maintained by intestinal conditions, which are distinctly affected by diet. The first symptom that appears when the balance is disrupted is inflammation. Inflammation is the body's first response in an effort to restore balance. If that balance is not restored, it will progress to a disease in which the pathogenic or opportunistic bacteria outnumber the beneficial bacteria.

There is a further desire in the poultry industry for methods to prevent avian disease that are considered natural, herbal or organic remedies. As such, it would be beneficial in the industry to develop natural avian treatments that are able to act in a preventative manner toward a wide range of infectious diseases, internal and external parasites, and environment-related problems. It would be further desirable that these treatments would include additional natural ingredients to aid in egg development, building improved immunity and growth in the young, respiratory and digestive health, and to counteract the deleterious effects of parasitic and pathogenic exposure, mating, brooding, pecking order, season change, transporting and other stress inducing events. The present invention is directed to an avian feed composition to be used as a trophorestorative that restores structure and function to reduce the risk of pathogens and parasites that destroy the balance of internal management of good health. When this balance is destroyed, disease and poor quality of internal function result.

SUMMARY OF THE INVENTION

In a first aspect, the present invention contemplates an avian feed composition comprising: apple cider vinegar; and garlic wherein the garlic is contacted with the apple cider vinegar for at least two weeks so that a maximum amount of garlic constituents are extracted into the apple cider vinegar.

This aspect may be further characterized by one or any combination of the following features: the feed further comprises eggshell powder; the feed further comprises dandelion leaf; the feed further comprises nettles; the feed further comprises St. John's wort; the feed includes an additional ingredient selected from the group consisting of: eggshells, goldenseal, osha, butterfly weed, yarrow, yellow dock, slippery elm, mullein, couch grass, horsetail, wild cherry bark, solomon's seal, staghorn sumach, Queen Anne's lace, barberry, rose hips, hawthorn berries, fennel, oats, ginger, yeast, honey, and any combination thereof; the feed includes an additional ingredient selected from the group consisting of: nettles, dandelion, comfrey, marshmallow, echinacea, St. Johns wort, white pine, alfalfa, chicory, burdock, chamomile, thyme, sage, wormwood, yarrow, calendula, mullein, plantain, lambs quarters, raspberry leaf, wild bergamot, chickweed, cleavers, rue, boneset eupatorium, red clover, lemon balm, violets, ground ivy, New England aster, strawberry leaf, peppermint, parsley, fennel, dill, corn silk, catnip, oregano, oats, ginger and any combination thereof.

In a second aspect, the present invention contemplates a method for preventing avian infection comprising: contacting one or more herbs with water for a period of time sufficient to transfer beneficial extracts from the herbs to the water to create an herbal extract, wherein the one or more herbs are selected from the group consisting of: yarrow, calendula, goldenrod, mullein, plantain, lambs quarters, raspberry leaf, wild bergmont, chickweed, cleavers, rue, boneset eupatorium, red clover, lemon balm, violets, ground ivy, New England aster, strawberry leaf, peppermint, parsley, fennel, dill, corn silk, catnip, oregano, oats, ginger, and any combination thereof; contacting garlic and one or more additional ingredients with vinegar for a time sufficient to transfer beneficial extracts from the additional ingredients to the vinegar to create a vinegar extract, wherein the one or more additional ingredients are selected from the group consisting of: yeast, raw honey, acetic acid, eggshell powder, goldenseal, osha, butterfly weed, yarrow, yellow dock, slippery elm, mullein, couch grass, horsetail, wild cherry bark, solomon's seal, staghorn sumach, Queen Anne's lace, barberry, rose hips, hawthorn berries, fennel, oats, ginger, and any combination thereof; combining the herbal extract with the vinegar extract in a ratio of about 10:1 to about 20:1 herbal extract to vinegar extract.

This aspect may be further characterized by one or any combination of the following features: the ratio of garlic to vinegar is about one to 6 cloves of garlic to about 0.5 to about 2 liters of vinegar.

In another aspect, the present invention contemplates a method for preventing avian infection comprising: monitoring and recording standard water intake of one or more birds over a period of at least 3 days; formulating a first batch of tonic with a garlic to vinegar ratio of 3 cloves of garlic to 1 liter of vinegar, wherein additional ingredients are also added to the first batch of tonic, the one or more additional ingredients being selected from the group consisting of: yeast, raw honey, acetic acid, eggshell powder, goldenseal, osha, butterfly weed, yarrow, yellow dock, slippery elm, mullein, couch grass, horsetail, wild cherry bark, solomon's seal, staghorn sumach, Queen Anne's lace, barberry, rose hips, hawthorn berries, fennel, oats, ginger, and any combination thereof; allowing the garlic, vinegar, and additional ingredients to remain in contact for at least two weeks; adding about 60 ml to about 350 ml of the first batch of tonic to about 3.5 liters of water to create a first tonic/water mixture; providing the first tonic/water mixture to the one or more birds; monitoring and recording the first tonic/water mixture intake of the one or more birds; comparing standard water intake with first tonic/water mixture intake; formulating a second batch of tonic with an increased garlic to vinegar ratio if the one or more birds shows increased first tonic/water intake as compared to standard water intake or formulating a second batch of tonic with a decreased garlic to vinegar ratio if the one or more birds shows decreased first tonic/water intake as compared to standard water intake; adding about 60 ml to about 350 ml of the second batch of tonic to about 3.5 liters of water to create a second tonic/water mixture; providing the second tonic/water mixture to the one or more birds.

This aspect may be further characterized by one or any combination of the following features: prior to creating the first or second tonic/water mixture, the water is contacted by one or more herbs for a period of time sufficient to transfer beneficial extracts from the herbs to the water to create an herbal extract, wherein the one or more herbs are selected from the group consisting of: nettles, dandelion, comfrey, marshmallow, echinacea, St. Johns wort, white pine, alfalfa, chicory, burdock, chamomile, thyme, sage, wormwood, yarrow, calendula, mullein, plantain, lambs quarters, raspberry leaf, wild bergamot, chickweed, cleavers, rue, boneset eupatorium, red clover, lemon balm, violets, ground ivy, New England aster, strawberry leaf, peppermint, parsley, fennel, dill, corn silk, catnip, oregano, oats, ginger, and any combination thereof; prior to creating the first or second tonic/water mixture, the vinegar is contacted by one or more additional ingredients for a time sufficient to transfer beneficial extracts from the additional ingredients to the vinegar to create a vinegar extract, wherein the one or more additional ingredients are selected from the group consisting of: yeast, raw honey, acetic acid, eggshell powder, goldenseal, osha, butterfly weed, yarrow, yellow dock, slippery elm, mullein, couch grass, horsetail, wild cherry bark, solomon's seal, staghorn sumach, Queen Anne's lace, barberry, rose hips, hawthorn berries, fennel, oats, ginger, and any combination thereof; formulating a third batch of tonic with an increased or decreased garlic to vinegar ratio; adding St. John's wort to the tonic.

In yet another aspect, the present invention contemplates a method for preventing avian infection comprising; monitoring and recording standard water intake of one or more birds over a period of at least 3 days; formulating a first batch of tonic with a garlic to vinegar ratio of 3 cloves of garlic to 1 liter of vinegar; adding one or more additional ingredients to the first batch of tonic, wherein the additional ingredients are selected from the group consisting of: yeast, raw honey, acetic acid, eggshell powder, goldenseal, osha, butterfly weed, yarrow, yellow dock, slippery elm, mullein, couch grass, horsetail, wild cherry bark, solomon's seal, staghorn sumach, Queen Anne's lace, barberry, rose hips, hawthorn berries, fennel, oats, ginger, and any combination thereof; allowing the garlic, vinegar, and one or more additional ingredients to remain in contact for at least two weeks; adding about 60 ml to about 350 ml of the first batch of tonic to about 3.5 liters of water to create a first tonic/water mixture, wherein prior to addition of the first batch of tonic to the water, the water is contacted by one or more herbs for a period of time sufficient to transfer beneficial extracts from the herbs to the water to create an herbal extract, wherein the one or more herbs are selected from the group consisting of: nettles, dandelion, comfrey, marshmallow, echinacea, St. Johns wort, white pine, alfalfa, chicory, burdock, chamomile, thyme, sage, wormwood, yarrow, calendula, mullein, plantain, lambs quarters, raspberry leaf, wild bergamot, chickweed, cleavers, rue, boneset eupatorium, red clover, lemon balm, violets, ground ivy, New England aster, strawberry leaf, peppermint, parsley, fennel, dill, corn silk, catnip, oregano, oats, ginger, and any combination thereof; providing the first tonic/water mixture to the one or more birds; monitoring and recording the first tonic/water mixture intake of the one or more birds; comparing standard water intake with first tonic/water mixture intake; formulating a second batch of tonic with an increased garlic to vinegar ratio if the one or more birds shows increased first tonic/water intake as compared to standard water intake or formulating a second batch of tonic with a decreased garlic to vinegar ratio if the one or more birds shows decreased first tonic/water intake as compared to standard water intake; adding one or more additional ingredients to the second batch of tonic, wherein the additional ingredients are selected from the group consisting of: yeast, raw honey, acetic acid, eggshell powder, goldenseal, osha, butterfly weed, yarrow, yellow dock, slippery elm, mullein, couch grass, horsetail, wild cherry bark, solomon's seal, staghorn sumach, Queen Anne's lace, barberry, rose hips, hawthorn berries, fennel, oats, ginger, and any combination thereof; adding about 60 ml to about 350 ml of the second batch of tonic to about 3.5 liters of water to create a second tonic/water mixture; providing the second tonic/water mixture to the one or more birds.

DETAILED DESCRIPTION

In general, the invention herein contemplates an avian feed composition and a method for administering the feed composition to one or more birds. The feed composition aids in preventing infection and illness including parasitic infestation. The feed composition's primary actions are nutritive, adaptogenic, alternative, astringent, bitter, diuretic, relaxant, and nervine. Additional actions are anthelmentic, anti-inflammatory, antibiotic, antiviral, antifungal, antimicrobial, antiseptic, carminative, pectoral, expectorant, laxative, lymphatic and rubefacient.

The present invention provides a method for maximizing the levels and efficacy of the antibiotic characteristics of garlic. More specifically, the feed composition of the present invention maximizes the potency of certain garlic components including but not limited to allicin and ajoene. The feed composition further includes additional natural ingredients that support disease prevention in avian species. The present invention further provides a method for analyzing avian behavior to determine the ideal formulation for an avian feed composition.

The process for preventing infection and illness in avian species begins by monitoring standard water intake by one or more birds over a period of time. This allows for a baseline from which to monitor if a flock's water intake has increased or decreased based on the formulation of a feed composition added to the flock's water. Ingredients that may be contained in the feed composition include, but are not limited to, garlic, apple cider vinegar, yeast, raw honey, acetic acid, eggshell powder, goldenseal, osha, butterfly weed, yarrow, yellow dock, slippery elm, mullein, couch grass, horsetail, wild cherry bark, solomon's seal, staghorn sumach, Queen Anne's lace, barberry, rose hips, hawthorn berries, fennel, oats, ginger, and any combination thereof. Preferred ingredients are selected from the group consisting of garlic, apple cider vinegar, and any combination thereof.

The feed composition is generally in the form of a liquid tonic and is added to water for intake by one or more birds. Preferably, from about 5 ml to about 100 ml of the tonic is added per one liter of water. More preferably, the amount of tonic added to per liter of water is from about 10 ml to about 40 ml. Even more preferably, the amount of tonic added to the water is about 20 ml per liter of water.

In preferred embodiments, the water may be contacted with certain herbs prior to inclusion in the feed composition with the tonic. The herbs may be initially contacted with water for a sufficient amount of time to transfer beneficial extracts from the herbs to the water to create an herbal extract. The herbs may be contacted with the water for anywhere from about 8 hours to about 3 weeks. Preferably, the herbs are in contact with the water for anywhere from 2 days to 14 days. The herbs contacted with the water to make the herbal extract can be any herb with health benefits to avian species. Examples of herbs that may be included in the herbal extract include but are not limited to yarrow, calendula, goldenrod, mullein, plantain, lambs quarters, raspberry leaf, wild bergmont, chickweed, cleavers, rue, boneset eupatorium, red clover, lemon balm, violets, ground ivy, New England aster, strawberry leaf, peppermint, parsley, fennel, dill, corn silk, catnip, oregano, oats, ginger, and combinations thereof.

In preferred embodiments, the tonic is formulated by contacting vinegar with fresh garlic so that the beneficial garlic constituents can be extracted and their health benefits maximized. The garlic constituents having known health benefits include, but are not limited to ajoene, allicin, aliin, allixin, allyl mercaptan, allyl methyl thiosulfinate, allyl methyl trisulfide, allyl propyl disulfide, diallyl disulfide, diallyl heptasulfide, diallyl hexasulfide, diallyl pentasulfide, diallyl sulfide, diallyl tetrasulfide, diallyl trisulfide, dimethyl disulfide, dimethyl trisulfide, dipropyl disulfide, methyl ajoene, methyl allyl thiosulfinate, propylene sulfide, 2-vinyl-4H-1,3-dithiin, 2-vinyl-4H-1,2-dithiin, S-allyl cysteine, S-allyl cysteine sulfoxide, S-allyl mercapto, cysteine and combinations thereof. The health benefits from these garlic constituents include antibiotic, detoxifying and antioxidant characteristics in addition to cancer inhibition, reduction in blood glucose levels and cholesterol levels. Other functions include blood thinning and liver protection.

The tonic preferably includes apple cider vinegar and even more preferably, organic apple cider vinegar, in an effort to maintain the natural and organic nature of the feed composition as a whole. The organic apple cider vinegar is preferably made by fermentation of apple cider that includes acetic acid bacteria, such that the bacteria form ethanol in the presence of oxygen to cause the fermentation of the apple cider. Preferably, the acetic acid bacteria is in the form of acetobacter found in mother of vinegar created during the fermentation process.

The ratio of garlic to vinegar may be as low as about 1 clove of garlic to about 1 liter of vinegar. The ratio may also be as high as 1 bulb of garlic (about 12 cloves) to about 1 liter of vinegar. The amount of garlic added to the vinegar may be increased or decreased depending on the relative health level of a flock or the amount of tonic tolerated by the flock without reducing water intake. Preferably, the amount of vinegar used to formulate the tonic is from about 0.25 liters to about 3 liters. More preferably, the amount of vinegar is from about 0.5 to about 2 liters. In preferred embodiments, the vinegar is organic apple cider vinegar. The organic apple cider vinegar includes apple pulp and juice from crushed organic apples and yeast for fermentation. After 7 to 10 days of fermentation, the apple cider vinegar is preferably stored in sealed containers. Storage may be for multiple years, but it is recommended that the tonic be utilized within one year to maximize effectiveness. Containers for the tonic are preferably stored on their side in a cool dark area.

In one preferred embodiment, the tonic further includes additional natural ingredients in a suitable amount to aid in avian disease prevention and general avian health. The amount of each additional natural ingredient added to the tonic is generally from about 0.25 ml to about 200 ml. More preferably, the amount of each additional ingredient is from about 1 ml to about 20 ml. The additional natural ingredients may aid in improving flock egg-laying and chick development. The additional ingredients may further improve avian respiratory health, reduce parasite infection and/or improve a flock's ability to recover from seasonal changes including harsh winter temperatures.

The contacting of the vinegar, garlic, and additional ingredients to formulate the tonic is preferably for a period of about 24 hours to about 1 month. More preferably, the contacting step takes place for about 1 week to about 3 weeks. The potency of the tonic increases as contact time increases. The vinegar acts to extract and preserve the beneficial health qualities of the garlic and any additional ingredients. Without contacting the garlic with some preservative, the antibiotic and other health qualities of the garlic are broken down, usually within 24 hours. By contacting the garlic and additional natural ingredients with the vinegar, the disease preventive constituents can be extracted, isolated and preserved so that their benefits can be realized by a flock. During the extraction process, vinegar acts as a menstruum capable of extracting alkaloids and minerals, including a number of garlic constituents. Once the vinegar is made, a further extraction can be done with additional herbs, for example, with garlic.

While vinegar is capable of extracting constituents from a number of natural sources, vinegar may become unstable during extraction from some herbs because it extracts the water from plants and it is liable to vegetative decomposition. Therefore, it is preferable that water is used as a solvent to extract beneficial ingredients from a number of herbs, resulting in an herbal extract. However, while water is a highly capable solvent for extraction purposes, it is not capable of long-term preservation. The herbal extract may therefore be added to the other ingredients to ferment when making the vinegar.

A number of herbs will show improved extraction with a water solvent as a water-based extraction. These herbs include but are not limited to nettles, dandelion, comfrey, marshmallow, echinacea, St. Johns wort, white pine, alfalfa, chicory, burdock, chamomile, thyme, sage, wormwood, yarrow, calendula, mullein, plantain, lambs quarters, raspberry leaf, wild bergamot, chickweed, cleavers, rue, boneset eupatorium, red clover, lemon balm, violets, ground ivy, New England aster, strawberry leaf, peppermint, parsley, fennel, dill, corn silk, catnip, oregano, oats, ginger, and combinations thereof. A number of additional ingredients show improved extraction using vinegar as the solvent as a vinegar-based extraction. These additional ingredients include, but are not limited to garlic, eggshell powder, goldenseal, osha, butterfly weed, yarrow, yellow dock, slippery elm, mullein, couch grass, horsetail, wild cherry bark, solomon's seal, staghorn sumach, Queen Anne's lace, barberry, fennel, oats, ginger, and combinations thereof. In preferred embodiments, the water-based extraction is combined with the vinegar-based extraction to provide the avian feed composition.

A number of herbs can also be added to the tonic, either during the initial contact with the garlic or after the contacting step takes place. Such herbs may have additional avian health benefits including reduced risk of infection, improved respiratory health, improved digestive health, improved tolerance to environmental changes including extreme temperatures, humidity and changes in surroundings (e.g. traveling or change in home location). The amount of herbs added can vary depending on the sufficient amount required for realization of a health benefit. The amount of herbs added may be from about 0.2 ml to about 1000 ml.

The combination of the vinegar, garlic, additional natural ingredients and herbs results in improved ability to prevent infection and disease in avian species. The combination further results in improved reproduction, improved respiratory function, and improved ability to withstand environmental stresses. These results are believed unexpected and superior to results obtained by the use of only vinegar, only the garlic, or only the additional natural ingredients. Therefore a synergistic effect occurs when the vinegar, garlic, and any additional ingredients are combined and in contact for a specified period of time.

In preferred embodiments, the contacting step takes place in any non-metal container. Preferably, the container is plastic, ceramic or glass so that corrosion is not an issue.

In order to determine the appropriate ratio of garlic to vinegar within the tonic and the appropriate ratio of tonic to water, it is necessary to first monitor the standard water intake of one or more birds. Preferably, when adding tonic to a flock's water, the water/tonic intake of the birds will not decrease as compared to the standard water intake. Often a decrease in water intake indicates that the ratio of tonic to water is too high or that the ration of garlic to vinegar is too high. In either case, it may be necessary to monitor the tonic/water intake of a flock and to formulate new tonic/water mixtures if the flock shows a decrease in water intake. It may also be necessary to monitor a flock's tonic/water intake for an increase in water intake. Preferably, the tonic to water ratio and the garlic to vinegar ratio is maximized to the highest level that can be tolerated by the flock without resulting in reduced water intake. Accordingly, if a flock's tonic/water intake does not decrease as compared to its standard water intake, it may be necessary to formulate new tonic/water mixtures having an increased amount of tonic and/or an increased amount of garlic. A flock's tonic/water intake is preferably continuously monitored to watch for signs of an increase or decrease in tonic/water intake. Any change may be indicative of a health problem or may simply be in response to a change in environmental aspects. For example, a flock's tonic/water intake may increase in response to a change in season. Accordingly, the tonic to water ratio and the garlic to vinegar ratio may be altered according to any change in flock intake habits. The tonic to water ratio and garlic to vinegar ratio may also be varied according to any cyclical schedule (e.g. according to season change and/or times of increased risk of parasitic infection).

In the event that one or more birds does not respond to treatment and symptoms of reduced health persist, an undiluted tonic may be formulated and be given directly to the one or more birds via a dropper or the like. The tonic may be formulated as specified herein, but not provided in a mixture with water. Preferably, the undiluted tonic is provided to one or more birds in the amount of about 0.25 to about 1.5 ml at least once a day. More preferably, the dosage of the undiluted tonic is about 0.75 ml at least once a day. Initially, the undiluted tonic may be provided twice a day and then reduced to once a day as the one or more birds shows signs of improving health.

Preferably, tonic intake of the flock should be constantly monitored and the amount of tonic should preferably be evaluated on at least a weekly basis. Use of the tonic is preferably discontinued when health balance is achieved. A flock will likely indicate improved health by reducing tonic intake over a period of time. Preferably the tonic should be used when a flock shows signs of reduced health. In addition, the quality of the tonic/water mixture should also be monitored so that the mixture is replaced with fresh mixture if the quality of the mixture becomes compromised.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of, or even consist of, the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps. Likewise, any reference to "first" or "second" items is not intended to foreclose additional items (e.g., third, fourth, or more items); such additional items are also contemplated, unless otherwise stated.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints. The specification of ranges herein also contemplates individual amounts falling within the range. Thus, for example, a range of 10 to 15 contemplates individually the amounts of 10, 11, 12, 13, 14, and 15.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The invention claimed is:
1. A method comprising:
   a. monitoring and recording standard water intake of one or more birds over a period of at least 3 days;
   b. formulating a first batch of tonic with a garlic to vinegar ratio of 3 cloves of garlic to 1 liter of vinegar; wherein one or more additional ingredients are also added to the first batch of tonic, the one or more additional ingredients being selected from the group consisting of: yeast, raw honey, eggshell powder, goldenseal, osha, butterfly weed, yarrow, yellow dock, slippery elm, mullein, couch grass, horsetail, wild cherry bark, solomon's seal, staghorn sumach, Queen Anne's lace, barberry, rose hips, hawthorn berries, fennel, oats, ginger, St. John's wort and any combination thereof;

c. allowing the garlic, vinegar, and additional ingredients to remain contact for at least two weeks;
d. adding about 60 ml to about 350 ml of the first patch of tonic to about 3.5 liters of water to create a first tonic/water mixture;
e. providing the first tonic/water mixture to the one or more birds;
f. monitoring and recording the first tonic/water mixture intake of the one or more birds;
g. comparing standard water intake with first tonic/water mixture intake;
h. formulating a second batch of tonic with an increased garlic to vinegar ratio as compared to the first batch of tonic if the one or more birds shows increased first tonic/water intake as compared to standard water intake or formulating a second batch of tonic with a decreased garlic to vinegar ratio as compared to the first batch of tonic if the one or more birds shows decreased first tonic/water intake as compared to standard water intake;
i. adding about 60 ml to about 350 ml of the second batch of tonic to about 3.5 liters of water to create a second tonic/water mixture;
j. providing the second tonic/water mixture to the one or more birds.

2. The method of claim 1, wherein prior to creating the first or second tonic/water mixture, the water is contacted by one or more herbs for a period of time to create an herbal extract, wherein the one or more herbs are selected from the group consisting of: nettles, dandelion, comfrey, marshmallow, echinacea, St. John's wort, white pine, alphalfa, chicory, burdock, chamomile, thyme, sage, wormwood, yarrow, calendula, mullein, plantain, lambs quarters, raspberry leaf, wild bergamot, chickweed, cleavers, rue, boneset, eupatorium, red clover, lemon balm, violets, ground ivy, New England aster, strawberry leaf, peppermint, parsley, fennel, dill, corn silk, catnip, oregano, oats, ginger, and any combination thereof.

3. The method of claim 2, wherein prior to creating the first or second tonic/water mixture, the vinegar is contacted by one or more additional ingredients to create a vinegar extract, wherein the one or more additional ingredients are selected from the group consisting of: yeast, raw honey, acetic acid, eggshell powder, goldenseal, osha, butterfly weed, yarrow, yellow dock, slippery elm, mullein, couch grass, horsetail, wild cherry bark, Solomon's seal, staghorn sumach, Queen Anne's lace, barberry, rose hips, hawthorn berries, fennel, oats, ginger, and any combination thereof.

4. The method of claim 1, wherein prior to creating the first or second tonic/water mixture, the vinegar is contacted by one or more additional ingredients to create a vinegar extract, wherein the one or more additional ingredients are selected from the group consisting of: yeast, raw honey, acetic acid, eggshell powder, goldenseal, osha, butterfly weed, yarrow, yellow dock, slippery elm, mullein, couch grass, horsetail, wild cherry bark, Solomon's seal, staghorn sumach, Queen Anne's lace, barberry, rose hips, hawthorn berries, fennel, oats, ginger, and any combination thereof.

5. The method of claim 1, further comprising formulating a third batch of tonic with an increased or decreased garlic to vinegar ratio as compared to the second batch of tonic.

6. The method of claim 1, wherein the one or more additional ingredients of part (b) includes eggshell powder.

7. The method of 1, wherein the one or more additional ingredients includes dandelion root.

8. The method of claim 1, wherein the one or more additional ingredients of part (b) includes nettles.

9. The method of claim 1, wherein the one or more additional ingredients of part (b) includes St. John's wort.

10. The method of claim 1, wherein an herbal extract is combined with the vinegar extract, the herbal extract comprising water contacted with yarrow, calendula, goldenrod, mullein, plantain, lambs quarters, raspberry leaf, wild bergmont, chickweed, cleavers, rue, boneset eupatorium, red clover, lemon balm, violets, ground ivy, New England aster, strawberry leaf, peppermint, parsley, fennel, dill, corn silk, catnip, oregano, oats, ginger, and any combination thereof.

11. The method of claim 1, wherein the vinegar is apple cider vinegar.

12. The method of claim 1, wherein the additional ingredients include eggshell powder, dandelion root, and St. John's wort.

* * * * *

UNITED STATES PATENT AND TRADEMARK OFFICE
CERTIFICATE OF CORRECTION

PATENT NO. : 8,372,446 B2
APPLICATION NO. : 12/416181
DATED : February 12, 2013
INVENTOR(S) : Susan Burek It is certified that error appears in the above-identified patent and that said Letters Patent is hereby corrected as shown below:

Col. 9, Claim 1, Line 2, after "remain" insert --in--

Col. 9, Claim 1, Line 3, "patch" should be "batch"

Signed and Sealed this
Twenty-sixth Day of March, 2013

Teresa Stanek Rea
*Acting Director of the United States Patent and Trademark Office*